United States Patent
José Prins et al.

(10) Patent No.: US 11,471,077 B2
(45) Date of Patent: Oct. 18, 2022

(54) BIOSENSOR WITH A GAP REGION FOR CONTINUOUS MONITORING

(71) Applicant: Technische Universiteit Eindhoven, Eindhoven (NL)

(72) Inventors: Menno Willem José Prins, Rosmalen (NL); Stefano Cappelli, Zürich (CH)

(73) Assignee: Technische Universiteit Eindhoven, Eindhoven (NL)

( * ) Notice: Subject to any disclaimer, the term of this patent is extended or adjusted under 35 U.S.C. 154(b) by 643 days.

(21) Appl. No.: 16/489,016

(22) PCT Filed: May 2, 2018

(86) PCT No.: PCT/EP2018/061153
§ 371 (c)(1),
(2) Date: Aug. 27, 2019

(87) PCT Pub. No.: WO2018/158469
PCT Pub. Date: Sep. 7, 2018

(65) Prior Publication Data
US 2021/0290110 A1 Sep. 23, 2021

Related U.S. Application Data

(60) Provisional application No. 62/643,092, filed on Mar. 14, 2018, provisional application No. 62/466,826, filed on Mar. 3, 2017.

(51) Int. Cl.
*A61B 5/1455* (2006.01)
*A61B 5/145* (2006.01)
(Continued)

(52) U.S. Cl.
CPC .......... *A61B 5/1455* (2013.01); *A61B 5/0093* (2013.01); *A61B 5/1459* (2013.01);
(Continued)

(58) Field of Classification Search
CPC . A61B 5/1455; A61B 5/0093; A61B 5/14546; A61B 5/1459; A61B 2562/0233;
(Continued)

(56) References Cited

U.S. PATENT DOCUMENTS 6,134,461 A * 10/2000 Say ..................... C12Q 1/006
600/309
6,602,678 B2 8/2003 Kwon
(Continued)

FOREIGN PATENT DOCUMENTS

WO WO2016075226 5/2016
WO WO2016075229 5/2016
(Continued)

*Primary Examiner* — Dominic J Bologna
(74) *Attorney, Agent, or Firm* — Lumen Patent Firm

(57) ABSTRACT

A biosensing device for continuous monitoring of an analyte in a fluid matrix includes an electromagnetic excitation element [402], a biosensing surface [406], an opposing surface [410], a separation component [420,422], light collection optics [412], a light sensor [414], an image recording and analysis system [416], and an excitation control system [400]. The separation component is connected to the biosensing surface and to the opposing surface, forming a concave gap region [408] between the biosensing surface and the opposing surface. The biosensing surface comprises biosensing particles sensitive to electromagnetic signals from the electromagnetic excitation element, where an optical response of the biosensing particles to the electromagnetic signals is adapted to change in the presence of an analyte in the gap region. The light collection optics couple light emitted from the biosensing particles on the biosensing surface to the light sensor. The image recording and analysis system is connected to the light sensor and processes light signals from the biosensing particles to determine presence or absence or concentration of the analyte in the fluid matrix.

13 Claims, 10 Drawing Sheets

(51) Int. Cl.
*G01N 21/64* (2006.01)
*G01N 33/543* (2006.01)
*G01N 15/14* (2006.01)
*A61B 5/1459* (2006.01)
*A61B 5/00* (2006.01)
*G01N 15/06* (2006.01)
*G01N 15/10* (2006.01)

(52) U.S. Cl.
CPC ....... *A61B 5/14546* (2013.01); *G01N 15/147* (2013.01); *G01N 21/648* (2013.01); *G01N 21/6428* (2013.01); *G01N 21/6456* (2013.01); *G01N 33/54306* (2013.01); *G01N 33/54366* (2013.01); *A61B 2562/028* (2013.01); *A61B 2562/0233* (2013.01); *A61B 2562/0285* (2013.01); *G01N 2015/0693* (2013.01); *G01N 2015/1006* (2013.01)

(58) Field of Classification Search
CPC ...... A61B 2562/028; A61B 2562/0285; G01N 15/147; G01N 21/6428; G01N 21/6456; G01N 21/648; G01N 33/54306; G01N 33/54366; G01N 2015/0693; G01N 2015/1006
See application file for complete search history.

(56) References Cited

U.S. PATENT DOCUMENTS

| | | | |
|---|---|---|---|
| 7,291,497 | B2 | 11/2007 | Holmes |
| 2011/0188030 | A1* | 8/2011 | Verschuren ............ G01N 21/41 356/128 |
| 2012/0059232 | A1 | 3/2012 | Gross |
| 2017/0315115 | A1* | 11/2017 | Prins ................ G01N 33/54306 |
| 2017/0362645 | A1* | 12/2017 | Prins .................... G01N 33/543 |

FOREIGN PATENT DOCUMENTS

| | | |
|---|---|---|
| WO | WO2016096901 | 6/2016 |
| WO | WO2016096908 | 6/2016 |

* cited by examiner

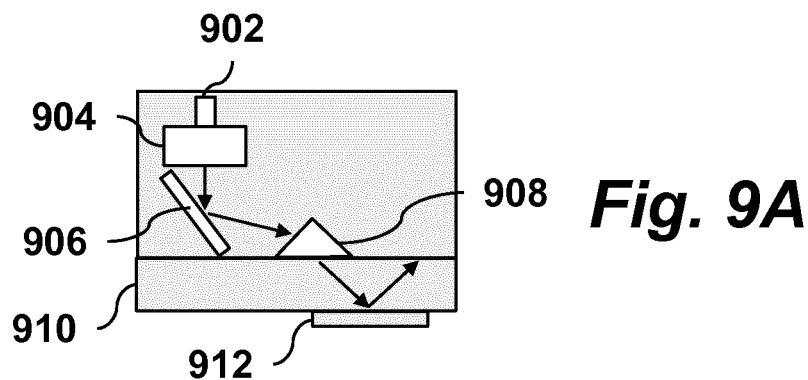
*Fig. 9A*
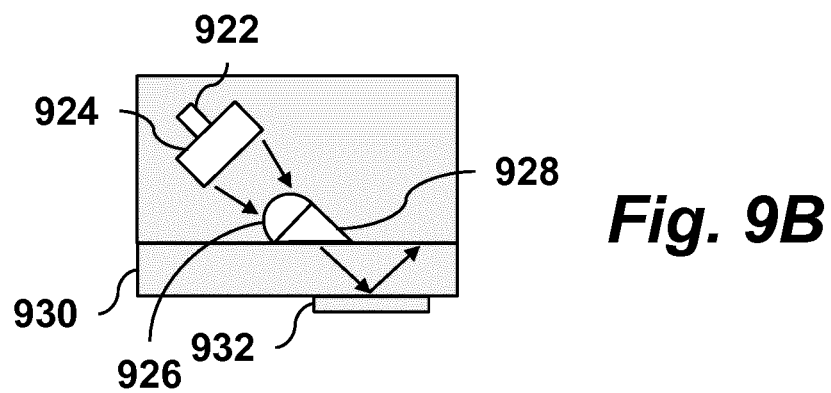
*Fig. 9B*
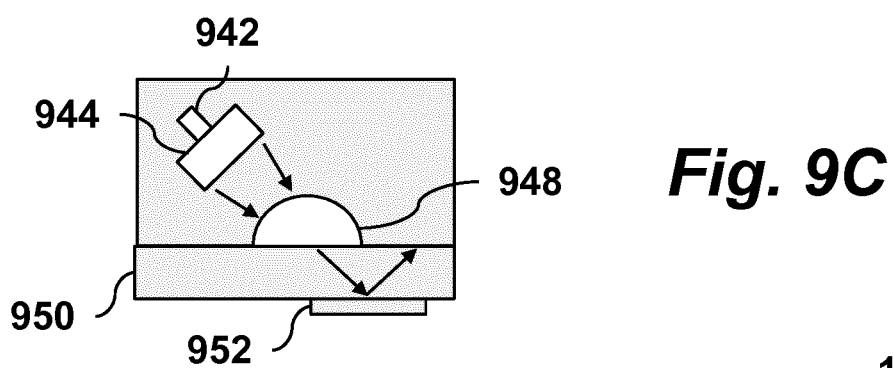
*Fig. 9C*
*Fig. 10*
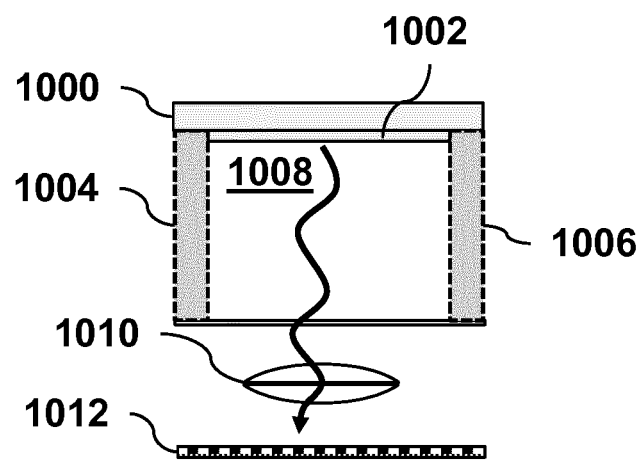

Fig. 14A
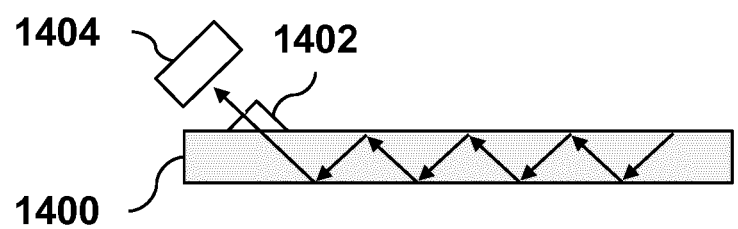
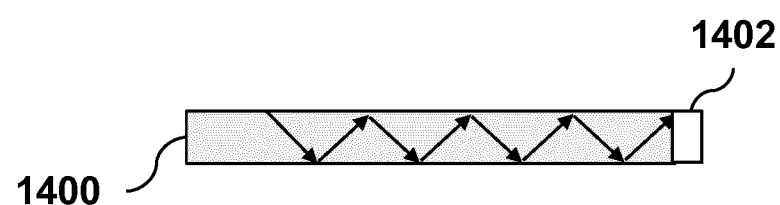
Fig. 14B

BIOSENSOR WITH A GAP REGION FOR CONTINUOUS MONITORING

CROSS-REFERENCE TO RELATED APPLICATIONS

This application is a 371 of PCT application PCT/EP2018/061153 filed May 2, 2018. PCT application PCT/EP2018/061153 claims the benefit of U.S. Provisional applications 62/466,826 filed Mar. 3, 2017 and 62/643,092 filed Mar. 14, 2018.

FIELD OF THE INVENTION

The invention relates generally to single particle continuous monitoring biosensor devices and methods.

BACKGROUND OF THE INVENTION

The following publications, which are incorporated herein by reference, relate to bio-detection by optical means, with a molecular mechanism that gives biomolecular specificity, and with an optical mechanism that transduces the molecular process into a detectable signal, typically by the use of particles and/or fluorescence: WO2016075226, WO2016096901, WO2016096908. WO2016075229. The optical mechanism can involve a change of scattering and/or absorption properties, a change of a coordination parameter of a particle, or a change of a fluorescence signal.

BRIEF SUMMARY OF THE INVENTION

The techniques described in these cited documents are intended for in-vitro and in-vivo biosensing. In all such applications, it would be advantageous if the sensor system can be miniaturized, for reasons of compactness, costs, convenience, low intrusiveness etc. For example, in several applications only limited space is available, particularly in cases where the sensor is used on or in a living biological system; e.g., for biosensing in/on/with a material or a device for support/actuation/stimulation/delivery in or on the body; e.g., a catheter, a patch, a tube, a needle, a fiber, a clip, a wire, a watch, an implanted probe, a pill, a subcutaneous strip, etc.; e.g., for temporary or for long-term use.

Furthermore, in-vivo and/or monitoring applications are demanding in terms of sensitivity, specificity, accuracy, signal stability, calibration, the measurement of time-dependent signals, and response times. Furthermore, in-vivo devices have difficult requirements regarding sterilization and sterility testing.

Another important aspect in all such applications is the transport process of the analyte to the sensing surface. In in-vitro diagnostics, the lateral transport of analyte toward the sensing surface is typically dominantly effectuated by advection, i.e., bulk motion of fluid, e.g., by bringing fluid into motion with a pumping principle.

In in-vivo applications, advective transport typically occurs when the biosensor is brought into contact with the matrix wherein the analyte is to be measured, e.g., when the sensor becomes exposed to interstitial fluid or to another biological fluid. Herein, a matrix is understood to mean an medium or material in which an analyte is dissolved or suspended. During initialisation, bulk fluid may enter the biosensor device. Thereafter, advective transport is not preferred as a transport mechanism, because mechanisms for generating advective transport complicate the device and can give unwanted mechanical perturbations of the in-vivo biological environment.

In in-vivo applications, diffusive transport processes are preferred, for device simplicity and minimal perturbation.

The invention relates to a continuous monitoring biosensor, specifically a miniature design with a mm-scale (or smaller) gap region between a biosensor surface and an opposing surface, sufficiently small that the matrix experiences significant diffusive transport in the biosensor region, which is important for in-vivo applications. Embodiments with a molecular separation component and various optical arrangements are also disclosed.

In one aspect, the invention provides device architectures for biomolecular continuous monitoring (BCM) with single-particle (SP) and/or single-molecule (SM) resolution, where the analyte diffuses towards the sensing surface and interacts with the particles, which are then detected and characterized by optical means. Solutions are given for making a miniaturized system that is suited for continuous monitoring, e.g., on or in the body.

Ideally, the front-end biosensing device can be scaled down—in at least one dimension—to a size of a few millimeters and also below 1 mm.

According to one aspect, the invention provides a biosensing device for continuous monitoring of an analyte in a fluid matrix. The device includes an electromagnetic excitation element, a biosensing surface, an opposing surface, a separation component, light collection optics, a light sensor, an image recording and analysis system, and an excitation control system. The separation component is connected to the biosensing surface and to the opposing surface, forming a concave gap region between the biosensing surface and the opposing surface, such that the biosensing surface and the opposing surface are opposite to each other and have a separation of at most 1 mm, wherein the biosensing surface and opposing surface both have lengths of at most 3 mm. The electromagnetic excitation element and the light sensor are positioned on opposite sides of the concave gap region. The excitation control system provides control signals to the electromagnetic excitation element to produce electromagnetic signals. The electromagnetic excitation element is optically coupled to the biosensing surface, and the biosensing surface comprises biosensing particles sensitive to the electromagnetic signals from the electromagnetic excitation element, wherein an optical response of the biosensing particles to the electromagnetic signals is adapted to change in the presence of an analyte in the gap region. The light collection optics couple light emitted from the biosensing particles on the biosensing surface to the light sensor; wherein the light sensor and light collection optics are positioned outside of the concave gap region. The image recording and analysis system is connected to the light sensor and processes light signals from the biosensing particles to determine presence or absence or concentration of the analyte in the fluid matrix.

In some embodiments of the biosensing device, the electromagnetic excitation element is optically coupled to the biosensing surface by the concave gap region. In some embodiments of the biosensing device, the electromagnetic excitation element is optically coupled to the biosensing surface by a waveguide. In some embodiments of the biosensing device, the concave region is an enclosed region, wherein the separation component comprises a porous material with pores of 500 nm or smaller. In some embodiments of the biosensing device, the concave region is an open region, with an entrance region opposite the separation component. In some embodiments of the biosensing device, the separation component rigidly connects to both the biosensing surface and to the opposing surface.

In some embodiments of the biosensing device, the biosensing surface and the opposing surface have widths of at most 1 cm. In some embodiments of the biosensing device, the opposing surface is optically transparent. In some embodiments of the biosensing device, the biosensing surface, the opposing surface, the separation component, the light collection optics, and the light sensor form a rigidly connected collection of components. In some embodiments of the biosensing device, the light sensor is a pixelated sensor chip, and wherein the image recording and analysis system comprises an input-output interface to the pixelated sensor chip. In some embodiments of the biosensing device, the light collection optics comprise a lens solidly integrated on the opposing surface, outside of the concave gap region. In some embodiments of the biosensing device, the electromagnetic excitation element is optically coupled to the biosensing surface by an optical waveguide providing total internal reflection or high angle illumination. In some embodiments of the biosensing device, the biosensing particles are micro- or nano-meter size biosensors with biomolecular specificity and single-molecule resolution.

BRIEF DESCRIPTION OF THE DRAWING FIGURES

FIGS. 2A-D are cross-sectional schematic diagrams of a biosensor device according to various embodiments of the invention.

Figure 3A:
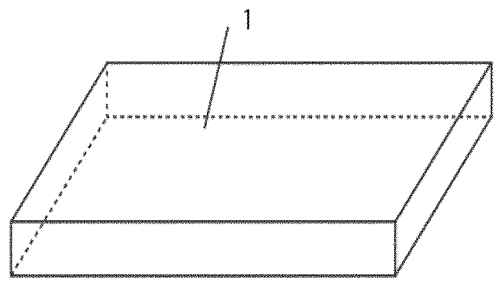

FIGS. 3A-B shows according to embodiments of the invention mounting options for the miniature biosensors, e.g. a patch (FIG. 3A), on a needle device (FIG. 3B), or an implant.

FIG. 3C shows a compact cube-like sensor device according to an embodiment of the invention.

Figure 4:
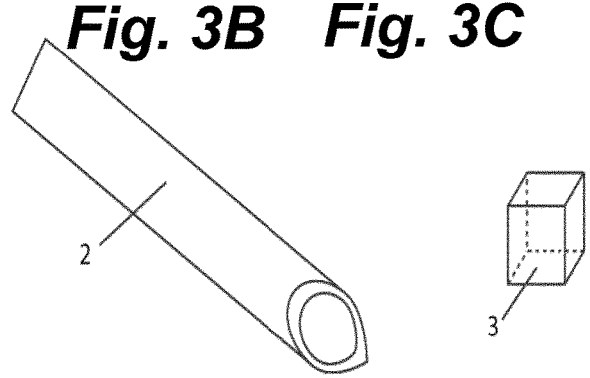
Figure 4:
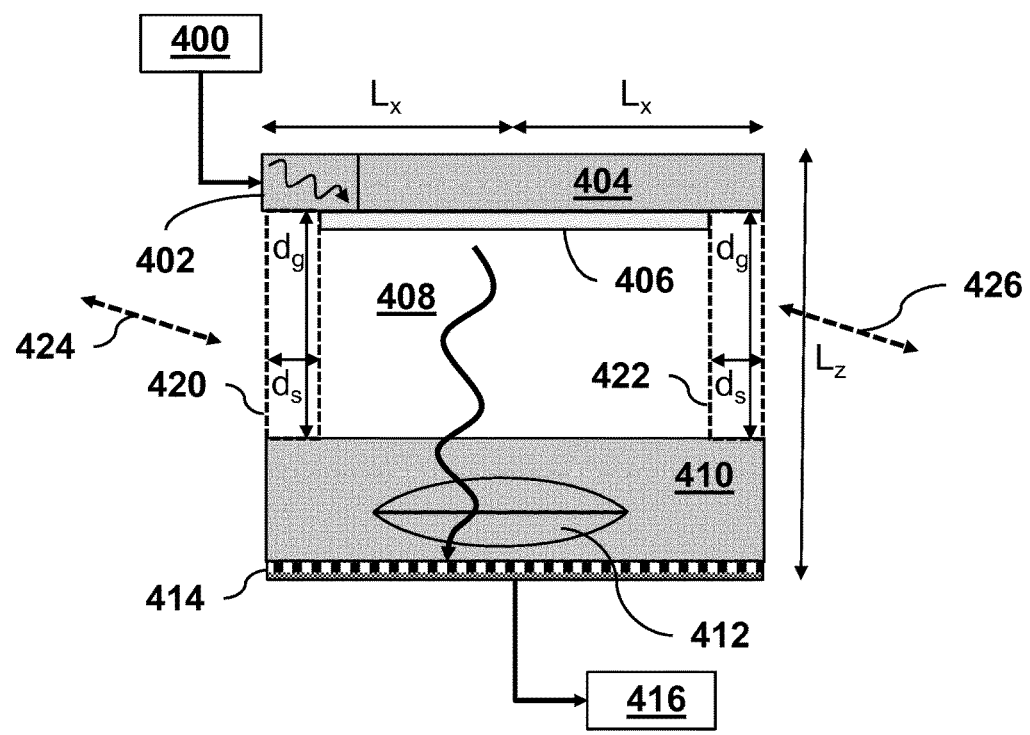

FIG. 4 is a cross-sectional schematic diagram of a biosensing device for continuous monitoring of an analyte in a fluid matrix according to an embodiment of the invention.

Figure 5:
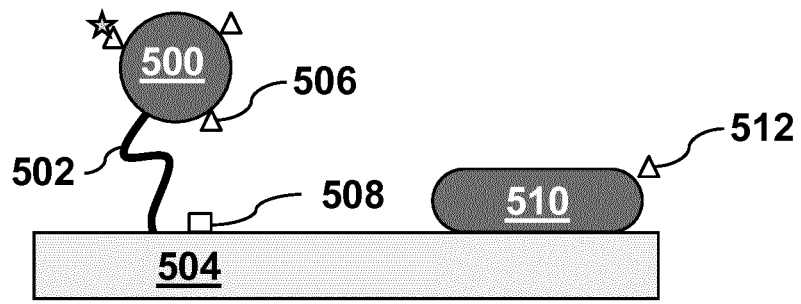

FIG. 5 is a schematic cross-sectional diagram detailing the molecular response layer of a device according to an embodiment of the invention.

Figure 6A:
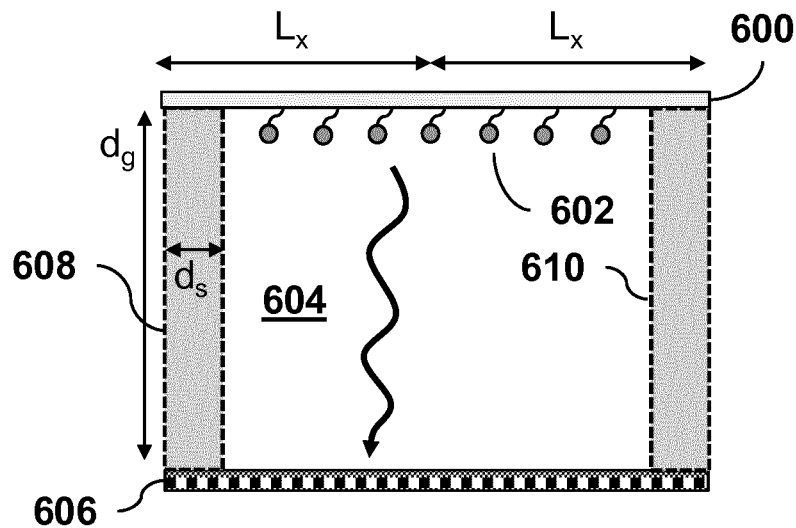

FIG. 6A is a cross-sectional schematic diagram using a selective membrane as a separation component according to an embodiment of the invention.

Figure 6B:
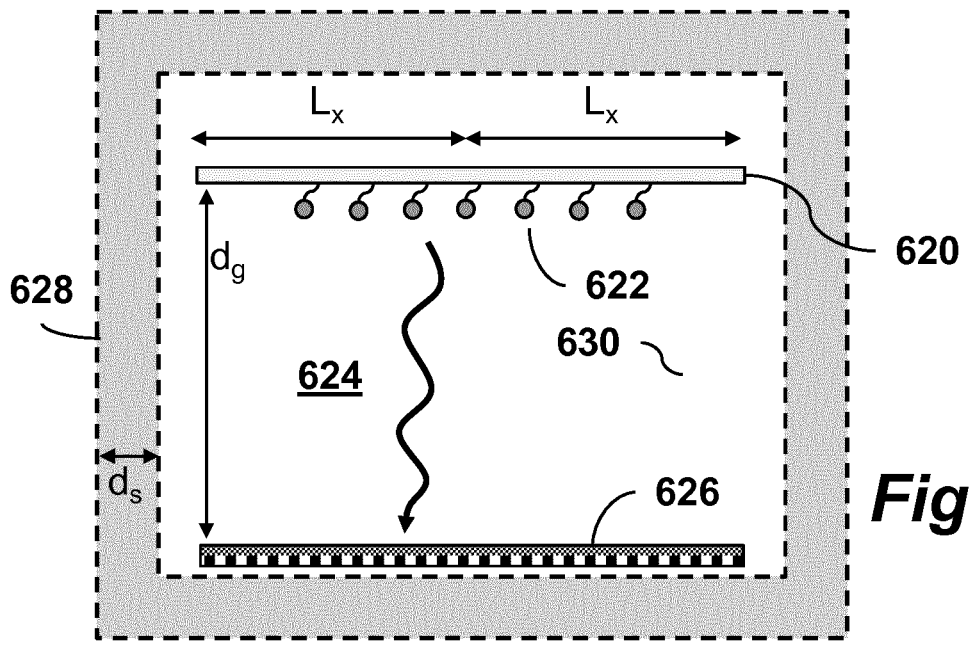

FIG. 6B shows the separation component be used to encapsulate the biosensing layer according to an alternate embodiment of the invention.

Figure 6C:
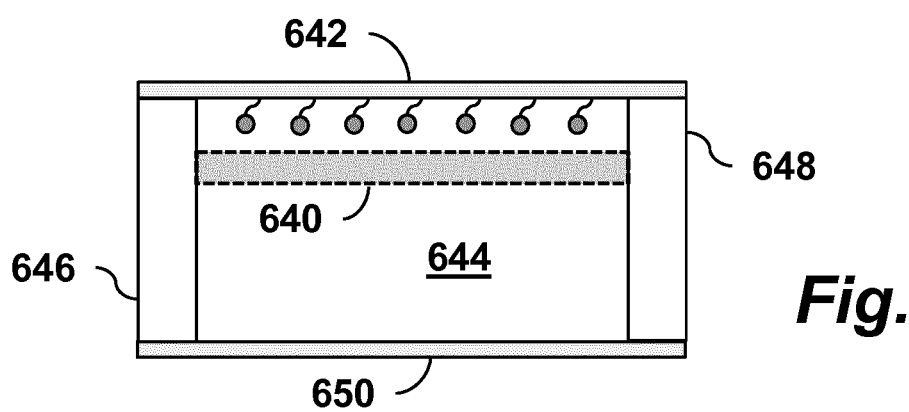

FIG. 6C shows a cross-sectional schematic diagram with a separation component 640 within the gap region 644 and parallel to the biosensing surface 642 according to an embodiment of the invention.

Figure 7:
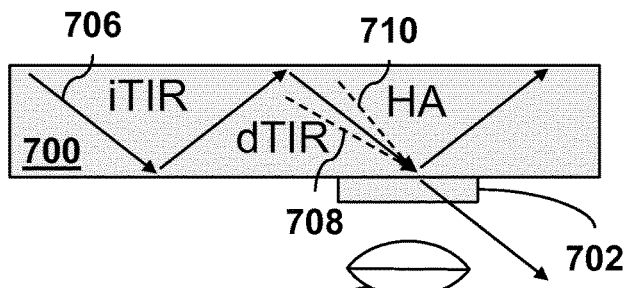

FIG. 7 provides according to an embodiment of the invention a schematic cross-sectional illustration of several possible strategies for optical excitation within a substrate 700.

FIGS. 8A-F shows various techniques for optical excitation and detection according to embodiments of the invention.

FIGS. 9A-C shows techniques for direct TIR excitation according to embodiments of the invention.

FIG. 10 is a cross-sectional schematic illustration of an embodiment of the invention using a set of lenses for imaging onto the sensor of the device.

Figure 11:
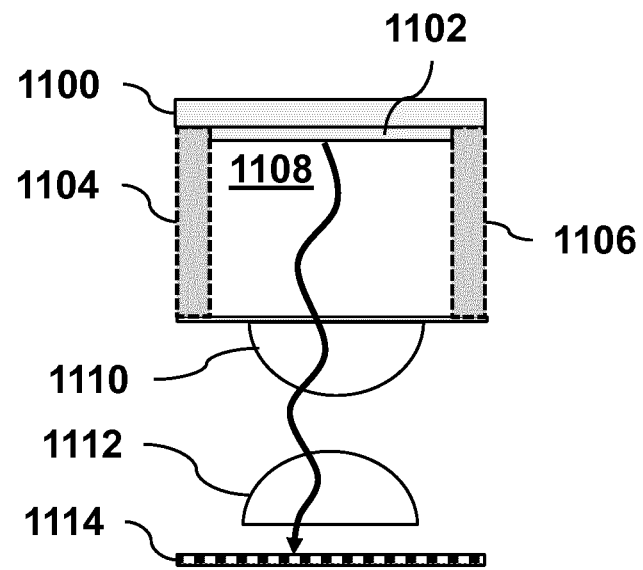

FIG. 11 is a cross-sectional schematic illustration of an embodiment of the invention using a set of rigidly coupled lenses for imaging onto the sensor of the device.

Figure 12:
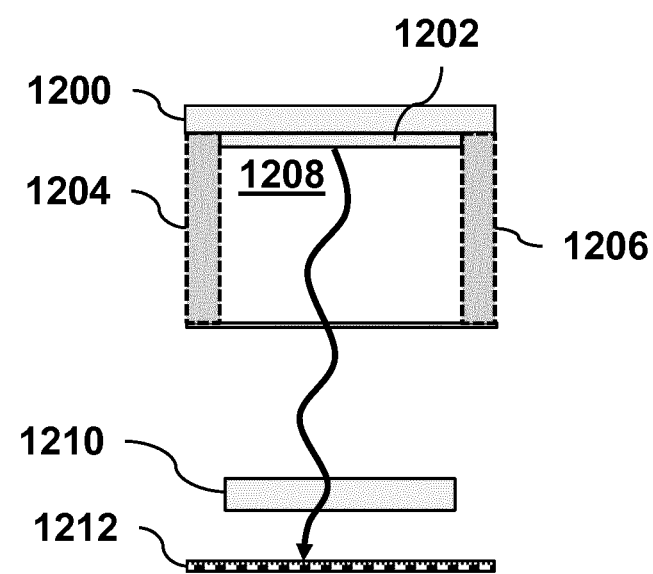

FIG. 12 is a cross-sectional schematic illustration of an embodiment of the invention using lensless imaging onto the sensor of the device.

Figure 13A:
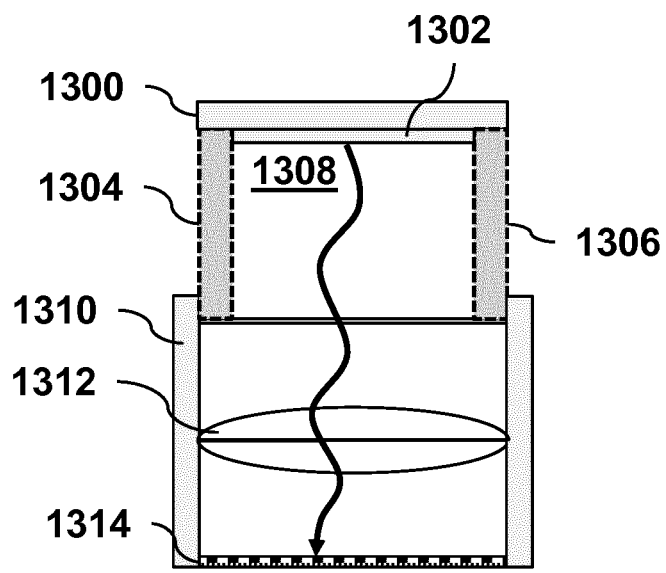
Figure 13B:
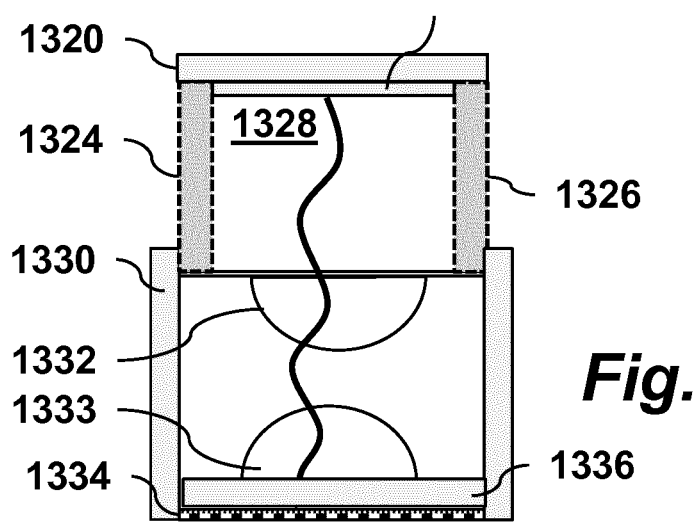
Figure 13C:
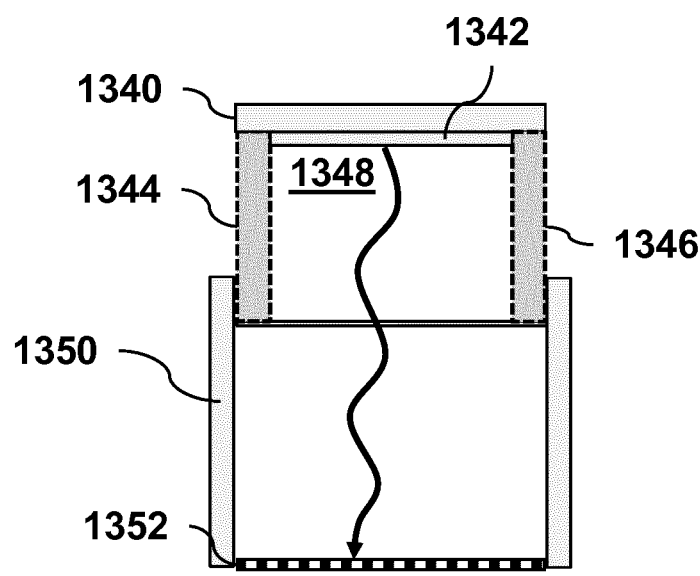

FIGS. 13A-C are cross-sectional schematic figures illustrating embodiments of the invention with examples of rigidly coupled imaging systems.

FIGS. 14A-B are cross-sectional views of parts of an embodiment of the invention, illustrating measurement of a reference light intensity.

DETAILED DESCRIPTION OF THE INVENTION

The inventors have realized that a sensor device with a cavity (with a "gap region") is advantageous for the optical system and—when designed with the right geometry—enables a sensor based on diffusive transport of target to the biosensing surface. Existing sensing geometries using a microfluidic device with a gap are designed to change the analyte concentration in the gap region by forced lateral bulk fluid transport. In contrast, embodiments of this invention use a gap device with design to enable sensing with diffusive analyte transport. Because diffusive transport is conventionally thought to be slow, this solution with a gap is counterintuitive, but it is surprisingly advantageous for monitoring applications, in-vivo applications, and for miniaturization, as will become evident from the embodiments discussed in detail below.

Figure 1A:
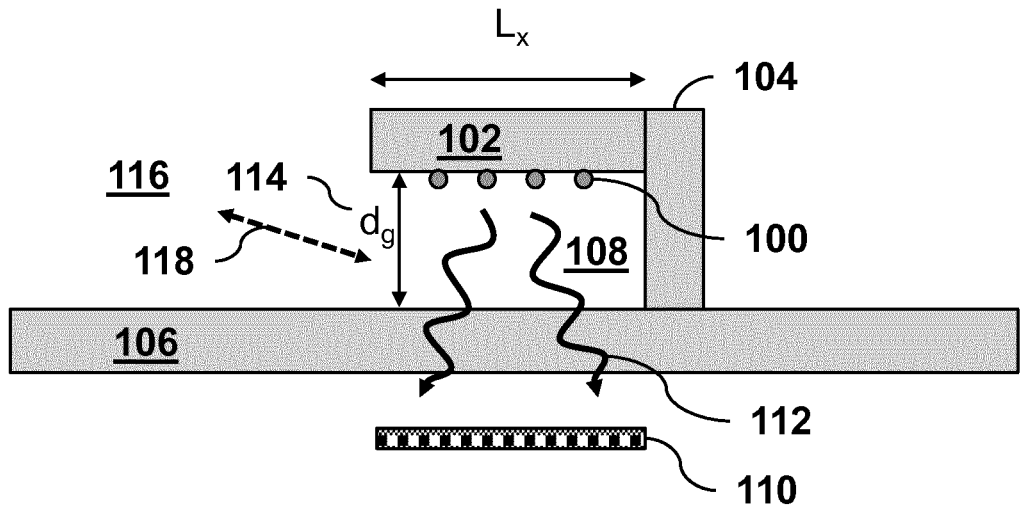
FIG. 1A shows a cross-sectional schematic diagram of an embodiment of the invention.

An embodiment of the invention is illustrated in the cross-sectional schematic diagram of FIG. 1A. The biosensing device has a gap region 108, which separates the biosensing surface 102 by a gap distance $d_g$ 114 from an opposite surface 106. A separation component 104 rigidly attached to surface 102 and surface 106 creates a third wall of the convex gap region 108. After excitation of biosensor particles 100 from the top, light 112 emitted from the biosensing surface 102 passes through the gap region 108 and through the opposite surface 106, onto a pixelated sensor chip 110. Thus, the total pathway of light, including electromagnetic excitation of the biosensing surface and light emitted from the biosensing surface to the sensor chip, propagates through the concave gap region, propagates through the opposite surface, and propagates through the light collection optics to the light sensor. The dashed arrow 118 indicates the exchange by diffusion of analyte in the matrix rather than by bulk flow of analyte between the contact matrix 116 outside and inside the gap region 108.

Figure 1B:
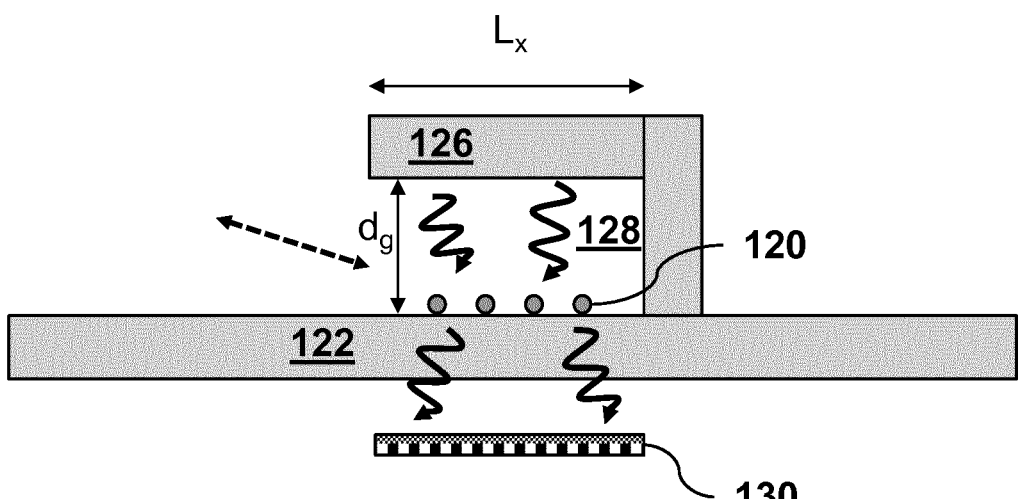
FIG. 1B is a cross-sectional schematic diagram of an alternative embodiment of the invention.

FIG. 1B is a cross-sectional schematic diagram of an alternative embodiment where the opposite surface 126 is positioned on the side of the gap region 128 where the excitation light originates, and the biosensing surface 122 with biosensor particles 120 is positioned on the side of the gap 128 where sensor chip 130 is positioned. As in FIG. 1A, also here the total pathway of light, including electromagnetic excitation of the biosensing surface and light emitted from the biosensing surface to the sensor chip, propagates through the concave gap region, propagates through the opposite surface, and propagates through the light collection optics to the light sensor. Compared to the embodiment of FIG. 1A, the embodiment of FIG. 1B is more restrictive in the design of the excitation system (due to the presence of the gap region in the excitation path), but has more freedom in the design of the sensing path (due to the absence of the gap region in the sensing path).

In the remainder of this document, embodiments will be sketched with a pathway as in FIG. 1A, with the understanding that the alternative configuration shown in the embodiment of FIG. 1B is a possible alternative as well.

The device is preferably a miniaturized optical biosensing device in which the biosensing surface is adapted for the measurement of specific targets in a contact matrix. The biosensing surface forms one wall of a concave gap region having an entrance region that allows diffusive exchange of analyte targets between the contact matrix inside and outside the gap region. The gap region allows lateral diffusive exchange of targets between the entrance region and the biosensing surface. Preferably, the gap region has an average gap thickness ($d_g$) and an average lateral diffusion length ($L_x$) toward the sensitive region of the sensing surface, where $L_x$ is 1 mm or less, and where $d_g$ is 1 mm or less. The biosensing surface preferably contains particles excited by electromagnetic excitation, and the light emitted by the particles is detected by the pixelated sensor chip and used to determine the presence and/or concentration of analyte targets in the contact matrix. The signal from the pixelated sensor chip preferably is analyzed at the level of individual particles, i.e., to provide single-particle resolution.

A first advantage of the biosensing device is a low background signal. For a biosensor in which signals are measured of a biosensing surface (a material that changes optical properties in dependence of analyte, e.g., a material that is non-uniformly present on the surface, e.g., in a form as small particles or as another spatial arrangement), the background is preferably as low as possible (preferably dark-field), e.g., with minimal scattering of excitation energy into the detection path. A design with excitation effectuated on one side of the gap region and light collection effectuated on an opposite side of the gap region helps to give low background due to the low refractive index of the aqueous material in the gap region, which gives low coupling.

A second advantage is that on one side of the gap region, a large space is available for the excitation components, and on the other side, a large space is available for the detection components. This gives spatial freedom and design freedom, which helps to optimize the two components and make an optimal total system. For example, lenses can be solidly integrated on the opposite side of the gap region without risking direct capture of excitation energy, because the excitation energy is situated on the particle side of the gap region. Also, the excitation can be designed, e.g., with optimal angles, solid angles, refraction, diffraction and/or wave-guiding properties, in large independence of the detection components on the opposite side of the gap region.

Figure 2A:
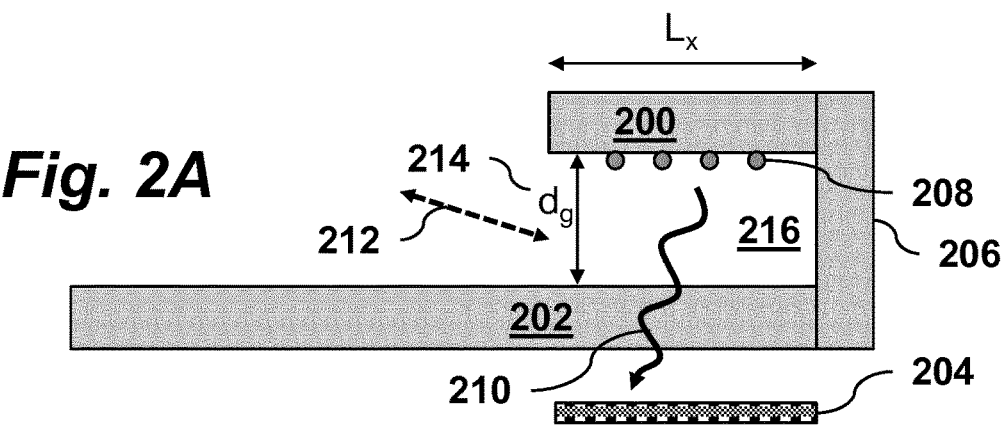

FIGS. 2A, 2B, 2C, 2D are cross-sectional schematic diagrams of a biosensor device according to various embodiments of the invention, illustrating various possible configurations. FIG. 2A shows an embodiment of a biosensing device with a gap region 216, which separates the biosensing surface 200 by a gap distance $d_g$ 214 from an opposite surface 202 that is extended laterally in one direction signaificantly farther than the length $L_x$ of the biosensing surface 200. A separation component 206 rigidly attached to surface 200 and surface 202 creates a third wall of the convex gap region 216. Light 210 emitted from biosensing particles 208 on the biosensing surface 200 passes through the gap region 216 and through the opposite surface 202, onto a pixelated sensor chip 204. The gap region 216, surface 202 and path between surface 202 and sensor 204 effectively function as light collection optics in this embodiment. In general, light collection optics is understood as including any medium through which light propagates from the biosensing surface to the sensor chip. The dashed arrow 212 indicates the exchange by diffusion of analyte into the gap region 216.

Figure 2B:
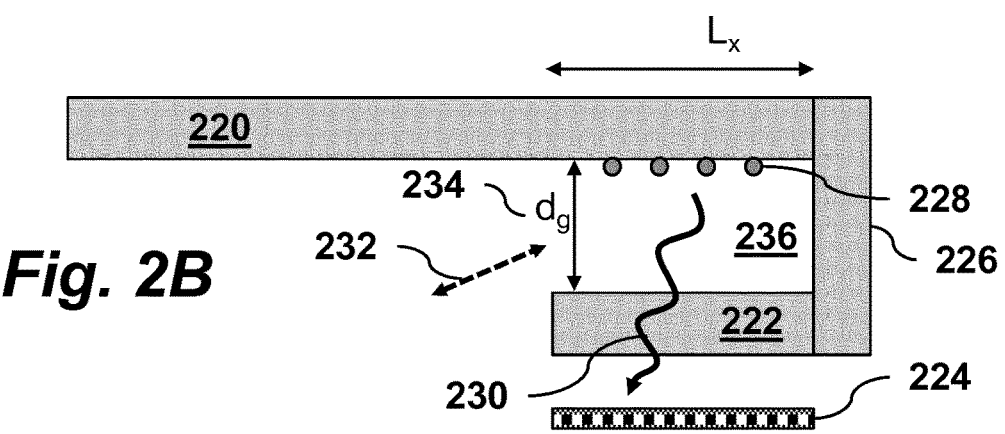

FIG. 2B shows an embodiment of a biosensing device with a gap region 236, which separates the biosensing surface 220 by a gap distance $d_g$ 234 from an opposite surface 222 that has a length $L_x$ corresponding to that of the actively biosensing length of the biosensing surface 220. The biosensing surface in this embodiment also has an inactive biosensing length extending substantially beyond the active length. A separation component 226 rigidly attached to surface 220 and surface 222 creates a third wall of the convex gap region 236. Light 230 emitted from biosensing particles 228 on the biosensing surface 220 passes through the gap region 236 and through the opposite surface 222, onto a pixelated sensor chip 224. The dashed arrow 232 indicates the exchange by diffusion of analyte into the gap region 236.

Figure 2C:
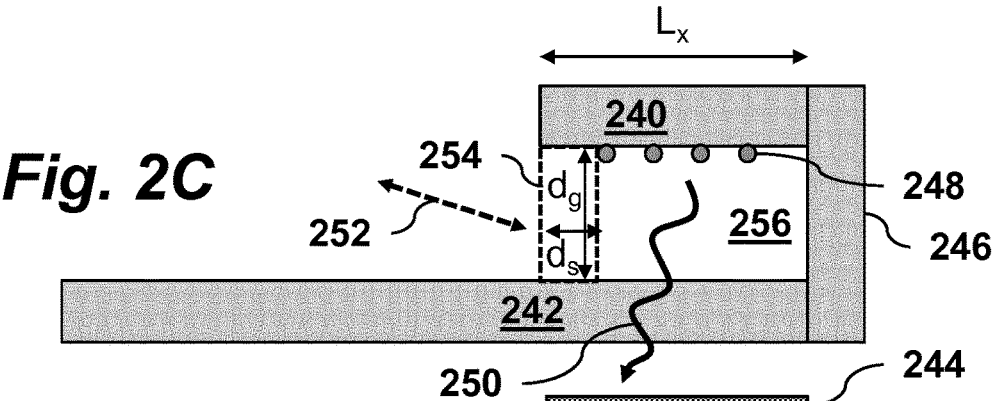

FIG. 2C shows an embodiment of a biosensing device with a gap region 256, which separates the biosensing surface 240 by a gap distance $d_g$ 254 from an opposite surface 242 that is extended laterally in one direction signaificantly farther than the length $L_x$ of the biosensing surface 240. A separation component includes wall 246 rigidly attached to surface 240 and surface 242 forming a third wall of the convex gap region 256. In this embodiment, the separation component also includes a fourth porous wall 254 (molecular separation component) of path-length $d_g$ through which analyte can diffuse into gap region 256. Light 250 emitted from biosensing particles 248 on the biosensing surface 240 passes through the gap region 256 and through the opposite surface 242, onto a pixelated sensor chip 244. The dashed arrow 252 indicates the exchange by diffusion of analyte into the gap region 256.

Figure 2D:
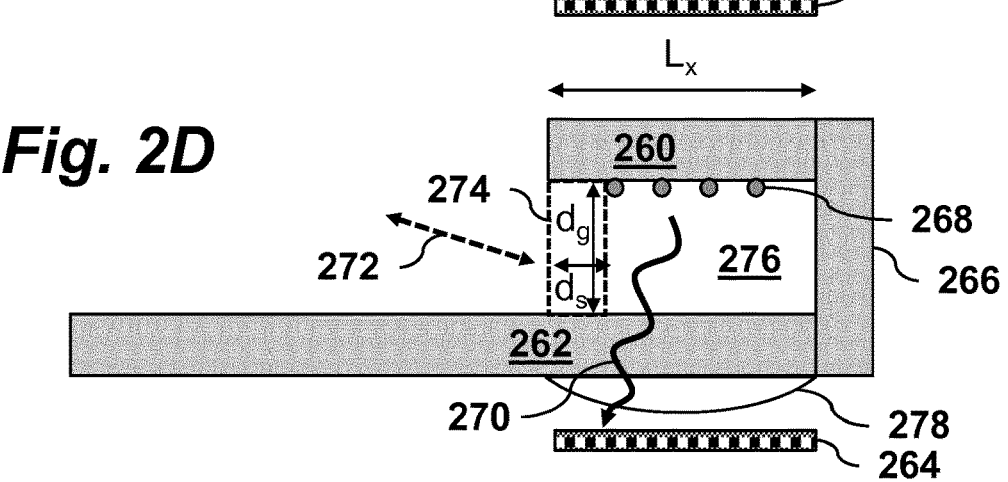

FIG. 2D shows an embodiment of a biosensing device with a gap region 276, which separates the biosensing surface 260 by a gap distance $d_g$ 274 from an opposite surface 262 that is extended laterally in one direction significantly farther than the length $L_x$ of the biosensing surface 260. A separation component includes wall 266 rigidly attached to surface 260 and surface 262 forming a third wall of the convex gap region 276. The separation component also includes a fourth porous wall 274 (molecular separation component) of path-length $d_s$ through which analyte can diffuse into gap region 276. Light 270 emitted from biosensing particles 268 on the biosensing surface 260 passes through the gap region 276 and through the opposite surface 262, onto a pixelated sensor chip 264. The dashed arrow 272 indicates the exchange by diffusion of analyte into the gap region 276. In this embodiment, the device includes a lens 278 as part of the light collection optics to collect emitted light and image it on the pixelated detection chip 264.

For a high signal to noise ratio, a preferred optical method is dark-field imaging, i.e., the light emitted from the sensing surface, e.g., by particles (e.g., scattering, fluorescence, luminescence, phosphorescence, etc.) is measured against a dark background. Excitation can be performed by using electric or electromagnetic fields, e.g., a light source. Then, the light emitted from the particles reaches the light detection sensor. The illumination pathway is designed to mainly illuminate the sensing surface, e.g., with particles, and to minimally generate optical scattering signals from the surroundings. Illumination methods are, e.g., total internal reflection (TIR) excitation and/or high angle (HA) illumination (as will be described in more detail below). An optical filter may be part of the system, e.g., before the detector in order to suppress signals due to excitation light.

An important aspect of biosensing devices is the transport of target or analyte to the sensing surface. Whilst in-vitro applications generally use lateral bulk transport by means of fluid actuation methods (e.g., pumping, capillary forces, or other bulk fluid actuation), in-vivo applications should minimally perturb the biological system on which the measurement takes place, i.e., minimal bulk material transport between the sensor and the biological system. Preferably, the biosensor device should be able to operate with diffusive material transport only.

In in-vivo applications, advective transport typically occurs when the biosensor is brought into contact with the matrix wherein the analyte is to be measured, e.g., when the sensor becomes exposed to interstitial fluid or to another biological fluid. During this initialization, bulk fluid may enter the biosensor device. The entry may be facilitated by a hydrophilic surface, a hygroscopic material, a gel, methods to lead air out (venting), methods to push air out, methods to generate, convert and solubilize gases, or other techniques.

However, after the initialization, strong advective transport is not preferred as a transport mechanism, because mechanisms for generating advective transport (e.g., a pumping mechanism) complicate the device and can give unwanted perturbations and displacements of the contact matrix and/or the in-vivo biological environment. Therefore, for in-vivo applications, diffusive transport processes are preferred, for device simplicity and minimal perturbation.

However, a problem is that diffusion is a slow transport process. Therefore, in-vivo sensing devices are typically designed with a geometry that gives maximal diffusive flux, e.g., by using a convex geometry (e.g., fiber tip) or a planar geometry (e.g., electrodes for electrochemical detection). According to common understanding, concave designs and designs with a deep and/or thin cavity are in principle disadvantageous for diffusive target transport toward a sensing surface. Surprisingly, the inventors have realized that a device design with a cavity (with a "gap region") is in principle advantageous for the optical system but in principle disadvantageous for the diffusive transport of target to the biosensing surface with particles. Although diffusion is a slow process, the inventors have realized that quasi-one-dimensional diffusion is a fast enough process to facilitate lateral transport of biological molecules, provided that the required diffusion distance is small enough.

The diffusion equation $\tau=L^2/D$ says that it takes a typical time $\tau$ for a target with diffusivity $D$ to diffuse across a distance $L$. For example: $L_D=100$ μm, $D=10^{-11}$ to $10^{-10}$ m²/s, gives $\tau=10^3$ to $10^2$ s. The inventors have realized that such time ranges are in principle suited for an in-vivo biosensor, i.e., in an acceptable time range for continuous monitoring of various typical biological processes.

The lower limit of L is the minimal size of the field-of-view. This is minimally a few times the diffraction limit of the system, which is around the wavelength of the light. Therefore, the lower limit of L is preferably on the order of a micrometer.

The inventors have realized that the above considerations allow a device design wherein target transport along the plane with sensing particles is diffusive rather than advective, and wherein optical detection occurs perpendicular to the lateral transport direction.

The length range is compatible with the typical desired device dimensions for in-vivo applications, where ideally the device needs to be scaled down to a size of a few millimeters and even below 1 mm, in at least one dimension.

Furthermore, embodiments of the invention provide a gap region with an average gap thickness ($d_g$) of 1 mm or less. A gap region with small $d_g$ has the following advantages: Variations in the contact matrix and biological environment can cause variable optical properties of the material in the gap region (e.g., refractive index, absorption), which can cause variabilities in the optical collection pathway (e.g., drift and noise). To minimize such variabilities it is advantageous to have a short optical path length through the gap region, i.e., small $d_g$. Small $d_g$ allows an optical detection pathway with a high numerical aperture and therefore a high light collection efficiency. Small $d_g$ allows a compact optical system, because the distance between the object plane (=sensitive region, e.g., with particles) and pixelated sensor chip can be small. Small $d_g$ allows a small distance between the object plane and the lens plane, which allows a high optical magnification for a given maximum total optical path length.

It should be noted that a temporal fluctuation of analyte concentration in the contact matrix can generate a spatial gradient of analyte concentration in the gap region, due to the fact that diffusive transport has a limited velocity. This may result in different response properties of different positions on the sensing surface. For example, particles near the entrance will be able to record rapid fluctuations of concentration whereas rapid fluctuations are damped out further from the entrance (i.e., deeper into the gap region). The position-dependent and time-dependent response of particles may be modeled and taken into account in signal processing, in order to get the most accurate determination of analyte concentration in the contact matrix.

A first function of the molecular separation component is to avoid that scattering objects (e.g., cells, cell fragments, microorganisms, aggregated proteins) appear in the gap region and/or in the vicinity of the biosensing particles, because scattering objects could generate background signals and false measurement signals. A typical passage size limit would be 500 nm, or 100 nm, or 50 nm. More generally, the molecular separation component has an internal structure with pores that allow the passage of specific target analytes but hinder the passage of other particles or substances that are undesired in the gap region.

A second function of the molecular separation component is to avoid that the sensing particles—in case they come loose from the biosensing surface—can be released into the biological system that is being monitored by the BCM unit. This needs to be suppressed because the release of particles could present a biological safety risk. A typical passage size limit of the separation component would be less than the size of the sensing particles.

A third function of the molecular separation component is to reduce the entry of unwanted molecules into the gap region, e.g., to reduce non-specific binding of molecules onto the particles, reduce the generation of non-specific signals, reduce optical effects in the gap region, etc. For the molecular filtering function, the molecular separation component may be e.g., a polymer or a gel, with selected pore size, physicochemical properties (e.g., charge, hydrophilicity/hydrophobicity), and/or biochemical properties (e.g., antifouling, attractive for certain proteins, biocompatibility).

The timescale of passage of the specific targets through the molecular separation component should be less than the required response time of the biosensor. The required response time depends on the application. It will typically be hours, parts of an hour, or minutes.

Embodiments of the invention may include optical elements mechanically connected to the biosensing surface, opposite surface, and sensor. For tuning purposes, one can integrate a moving component, e.g., an object or a lens or an imaging sensor mounted on a linear stage, or another component for adaptable optics, e.g., a liquid crystal device. For example, the motion of a component along the optical axis allows for the tuning of the focal plane with respect to the sensor plane, helping to form a sharp image of the object. Actuation systems such as voice-coil-motors (VCM) and silicon MEMS have already reached a good level of miniaturization (few millimeters) and reduced manufacturing costs.

On the other hand, in some embodiments of this invention, the particles to be imaged are fixed on a substrate with no or limited freedom of x-y movement, so that the distance from the image plane to the light sensor can be fixed and does not need to be adjustable. Furthermore, the particles do not need to be exactly in focus, because the biosensing signals relate to a change of coordination parameter or to a change of a spectral characteristic. This allows that small or slow mechanical variations of the biosensing surface with respect to the optical imaging components may still be present in the system, e.g., due to thermal or mechanical drift. Small or slow changes will be acceptable because the particles do not need to be exactly in focus for the biosensing functionality. Thus, the optical element(s), biosensing surface, opposite surface, and sensor are preferably mechanically and rigidly connected to each other.

Furthermore, many particles are attached to the surface and each particle functions as an independent biosensor. This gives redundancy in the system and therefore tolerance for uncertainties and for exclusion of particles in the analysis procedure, e.g., due to drift of optical conditions or parameters. Furthermore, collective drift can be corrected by measuring the average drift of the particles or by introducing fiduciary markers on the substrate.

Furthermore, miniaturization is advantageous to have low drift. Concerning for example thermal drift, a column with a length of 1 mm made of material with a thermal expansion coefficient of $10^{-4}$ $K^{-1}$ (e.g., polystyrene), expands by only 0.1 micrometer per degree.

Fixing the components rigidly together is beneficial for miniaturization, may decrease manufacturing costs, and will allow to create the device as a single robust and rigid device.

The preferred characteristics for a fixed-component system are as follows:

Depth of field, for low particle-to-particle cross-talk. Ability to image neighbouring particles independently. This requires a sufficient depth of field to accommodate for defocusing effects (and consequent particle-to-particle cross-talk) due to tolerance of distances and drift in the system.

Depth of field, in order to generate images of particles with a sufficient signal to noise ratio (SNR). The particles need to be imaged with enough statistics, e.g., with enough photon counts per imaged particle to be able to distinguish it from the background noise.

Magnification—number of pixels per imaged particle on the image sensor. For the detection of changes of particle motion, at least 2×2 pixels per particle are required; for the detection of changes of light intensity, at least 1 pixel per particle is required.

Depending on the miniaturization strategy, one or multiple biomolecular continuous monitoring (BCM) devices can be used in various ways. For example, miniature biosensors may be mounted on a patch (FIG. 3A), on a needle device (FIG. 3B), or an implant.

FIG. 3A shows a biosensor with a planar device geometry, which could be suited as a patch on the skin. Diffusive transport of analyte can occur in a direction perpendicular to the plane of the device and the axis of the optical sensing path can be along the plane of the device. FIG. 3B shows a longitudinal needle-type device. Diffusive transport of analyte can occur in a direction perpendicular to the shaft of the needle and the axis of the optical sensing path can be along the shaft of the needle. Alternatively, the diffusive transport of analyte can occur along the direction of the shaft and the axis of the optical sensing path can be perpendicular to the shaft of the needle. FIG. 3C shows a compact cube-like sensor device, which could be implanted into a biological system (e.g. in the skin) or which could be in direct contact with a biological fluid (e.g. saliva or another mucosal fluid), with an entry port for diffusional transport of analyte into the device and with an optical pathway for detection of analyte integrated in the device.

FIG. 4 is a cross-sectional schematic diagram of an embodiment of a biosensing device for continuous monitoring of an analyte in a fluid matrix. An electromagnetic excitation element 402 sends signals to an excitation control system 400 optically coupled to a top substrate 404 having a biosensing surface 406. The biosensing surface comprises biosensing particles sensitive to electromagnetic signals from the electromagnetic excitation element, where an optical response of the biosensing particles to the electromagnetic signals is adapted to change in the presence of an analyte in the gap region. An opposing surface 410 is separated by a concave gap region 408 from the biosensing surface 406 by a separation component comprising walls 420, and 422. Opposing surface 410 is formed by a substrate which includes light collection optics 412, which guides light to a light sensor 414, which sends signals to an image recording and analysis system 416 to determine presence or absence or concentration of the analyte in the fluid matrix.

Separation components 420, 422 may be composed of size-selective membrane or hydrogel that allows diffusion of target analyte 424, 426 into gap region 408 but blocks other particles. The separation component can be placed in proximity of the molecular response layer 406. Excitation light source unit 402 has a light source such as an integrated LED, SLD, etc., and optical components such as lenses, mirrors, prisms, etc., to direct the light through the substrate 404 into the responsive layer 406. Excitation can be performed both in the $L_x$ and $L_y$ directions. Substrate 404 has optical properties, e.g., glass or polymeric/plastic material, waveguide, through which the response layer 406 is excited. The substrate is transparent with respect to the light used to excite the molecular responsive layer 406. Moreover, for TIR excitation, there is a difference between the refractive indices of the substrate and of the medium of the molecular responsive layer, with the latter being the smaller one.

Molecular response layer or sensing surface 406 may contain capture molecules, enzymes, particles, fluorescent dyes, etc. This layer is exposed to components of the biological matrix of which biochemical and/or biological properties are to be sensed. Moreover, fiducial markers can be present in order to characterize/correct the signal emitted by the molecular response layer.

The molecular responsive layer is a material that changes optical properties in dependence on the presence of the target analyte. It can be a material that is non-uniformly present on the surface, with a spatial arrangement. The responsive layer may contain small particles that are spatially separated on the sensing surface, e.g., plasmonic particles or particles for tethered particle motion. The responsive layer may also be another spatial arrangement of sensing material, e.g., a pattern of optically responsive material, e.g., a pattern of material that changes spectral properties (e.g., fluorescence) or that changes scattering properties in dependence of analyte, e.g., a hydrogel with a spatial structure that can be imaged optically or otherwise detected.

Imaging element(s) 412 comprise one or multiple optical components, e.g., a single lens or a set of lenses, a light blocking element, an aperture, etc. A lens can have a 3-dimensional shape, or it can for example be a flat lens such as a Fresnel lens. The light emitted from the response layer 406 is focused on the light detection chip, i.e., the imaging sensor 414. The imaging sensor 414 typically has a sensitive layer that forms a flat plane; in that case the lenses 412 are typically aspheric lenses. Light detection chip 414 with pixels, e.g., CCD, CMOS, or another light sensitive electronic device, is connected to image recording and analysis system 416, which may include an Input/Output (I/O) interface to control the light detection chip.

Substrate 410 has optical properties to allow propagation of the light emitted from the biosensing surface. It contains the imaging system 412 and is mounted to the light detection chip 414. Preferably, the sensing surface 406, the optical component 412, and the imaging sensor 414 are rigidly connected to each other, so as to form a stable device. As further addition, the excitation light source unit 402 is rigidly connected to the abovementioned elements and can be placed in or on top of substrate 404.

The dimension $L_x$ is small enough so that the characteristic diffusion time of the analytes toward the biosensing surface 406 is smaller as compared to the characteristic time of the biological process that is to be monitored. The dimension $L_y$ is determined by the desired miniaturization specifications of the device, typically less than 1 cm or less than 1 mm. In this way, multiple sensing units can be placed in parallel for control/multiplexing in a single device.

FIG. 5 is a schematic cross-sectional diagram detailing the molecular response layer of a device according to an embodiment of the invention. The biosensing layer may have various biosensing elements, such as an optically transparent substrate 504, e.g., glass/polymer/plastic; a linker/tether 502, e.g., a ssDNA, dsDNA, polymer; a particle 500 with micro- or nanometer size. The particle can be polymeric, metallic, inorganic (e.g., glass), semiconductor, etc.; a plasmonic particle 510, e.g., a gold nanorod; a fluorescent particle 506, 508, 512, e.g., a carbon nanotube. It also may involve the use of bio-molecular components, e.g., capture molecules, enzymes, antibodies, aptamers, fluorescent dyes, hydrogel, carbohydrates, nucleotides, peptides, polymer, etc. This gives the biomolecular specificity to the device. Bio-molecular components might include also conformation-changing molecules, e.g., proteins, polymers. Preferably, the device has single-particle and/or single-molecule resolution. Alternatively, the device may operate by recording cumulative or average signals from an ensemble of responsive particles and/or molecules.

FIG. 6A is a cross-sectional schematic diagram of an embodiment using a selective membrane as a separation component. Substrate 600 has biosensing particles 602 on its surface and forms a top wall of a gap region 604. A sensor 606 forms an opposite surface, formig the bottom wall of the gap, while separation components 608, 610 form side walls. The separation components may be composed of a selective membrane (e.g., size-selective) to prevent large objects, like white and red blood cells, to reach the molecular responsive layer 602 and generate a background signal. The analytes or targets are able to pass through the separation component, with thickness $d_s$, and are able to diffuse to the responsive layer. In this embodiment, the separation component is placed in close proximity to the sensing layer Alternatively the separation component be used to encapsulate the biosensing layer, as shown in FIG. 6B, which shows a cross-sectional schematic diagram illustrating an embodiment using a selective membrane as an encapsulating separation component. Substrate 620 has biosensing particles 622 on its surface and forms a top wall of a gap region 624. A sensor 626 forms an opposite surface, forming the bottom wall of the gap, while separation component 628 forms side walls. The separation components may be composed of a selective membrane (e.g., size-selective) to prevent large objects, like white and red blood cells, to reach the molecular responsive layer 622 and generate a background signal.

In both embodiments of FIGS. 6A and 6B, the separation component can be a membrane layer with pores that are large on the scale of molecules (e.g., 100 nm), or it can be made of a material with molecular-scale pores (e.g., a hydrogel). Furthermore, the membrane can contain catalytic elements, e.g., for the reduction of oxygen species or capturing of reactive oxygen species (ROS).

The analytes of interest can diffuse through the separation component and interact with the responsive layer. Although diffusion is a slow process, the inventors have realized that one-dimensional diffusion is a fast enough process to facilitate lateral transport of biological molecules, provided that the required diffusion distance ($d_s+L_x$) is small enough.

The diffusion equation $\tau=L^2/D$ says that it takes a typical time $\tau$ (for a target with diffusivity D to diffuse across a distance L. For example: $L_D=100$ μm, $D=10^{-11}$ to $10^{-10}$ m$^2$/s, gives $\tau=10^3$ to $10^2$ s. The inventors have realized that such time ranges are in principle suited for an in-vivo biosensor, i.e., in the same time range as typical biological processes that are to be monitored.

The diffusion time $\tau_s$ through the separation component is determined by the dimension of the analyte, the pore-size distribution and its thickness $d_s$. In general, this diffusion time should be smaller than the lateral diffusion time $\tau_s \ll \tau_x$.

FIG. 6C shows a cross-sectional schematic diagram illustrating an embodiment with a separation component 640 within the gap region 644 and parallel to the biosensing surface 642. The separation component 640 can be a semipermeable membrane, e.g. a size-selective membrane, that lets analyte molecules pass and blocks substances that can perturb the biosensing surface.

Due to the proximity of the separation component 640 to the biosensing surface 642, the total volume between separation component and biosensing surface is small, and therefore the response time is relatively fast even if the separation component has a low permeability for the analyte. Separation components 646 and 648 are connected to the biosensing surface 642 and to the opposing surface 650.

We now turn to various techniques for optical excitation and detection, which may be implemented together with various embodiments discussed above. The molecular process in the biosensing surface is transduced into a detectable signal with an optical mechanism. The optical mechanism can involve a change of scattering and/or absorption properties, a change of spectral properties, a change of a coordination parameter of a particle, or a change of a scattering intensity. In order to generate the optical signal, the optically reactive element of the responsive layer, i.e., mobile particles and/or plasmonic particles are optically excited by one of various techniques. These will be described in relation to the embodiment shown in FIG. 8A, which shows a cross-sectional schematic diagram of a device having an optical excitation element 800 and substrate 802 with optical properties, e.g., glass or polymeric/plastic material whose refractive index is greater than that of the medium surrounding the biosensing surface 804. It also includes separation components 806, 808, gap region 810, lower substrate 812 having opposite surface and containing optical element 814, and sensor 816.

For a high signal to noise ratio, the preferred imaging method is dark-field imaging, i.e., the signal emitted from sensing layer, e.g., from the particles, e.g., scattering, fluorescence, phosphorescence, luminescence, etc., is measured against a dark background. Excitation can be performed by using electric or electromagnetic fields, e.g., a light source. In the latter case, the illumination pathway is designed to mainly illuminate the sensing layer and to minimally generate optical scattering signals from the surroundings. Illumination methods are e.g., total internal reflection (TIR) excitation and/or high angle (HA) illumination. FIG. 7 provides a schematic cross-sectional illustration of several possible strategies for optical excitation within a substrate 700, namely:

1. Indirect total internal reflection (iTIR);
2. Direct total internal reflection (dTIR);
3. High angle illumination (HA).

Total internal reflection (TIR) occurs when the light 706 encounters an interface between a medium with high refractive index and a medium with lower refractive index (e.g., from glass to water, with $n_{glass}=1.51$ and $n_{water}=1.33$), with an angle of incidence 708 above a critical angle. Then, an evanescent field is generated in the position where the light is reflected. The intensity of the field depends on the refractive indices of the materials and the angle of illumination, and decays exponentially from the surface with a penetration depth that is related to the angle of incidence and to the wavelength of the light. If the angle of the incoming beam is below the critical angle 710, then the light can be transmitted through the molecular response layer 702 and propagate through subsequent optics 704. We will refer to this condition as high-angle (HA) excitation.

Figure 8A:
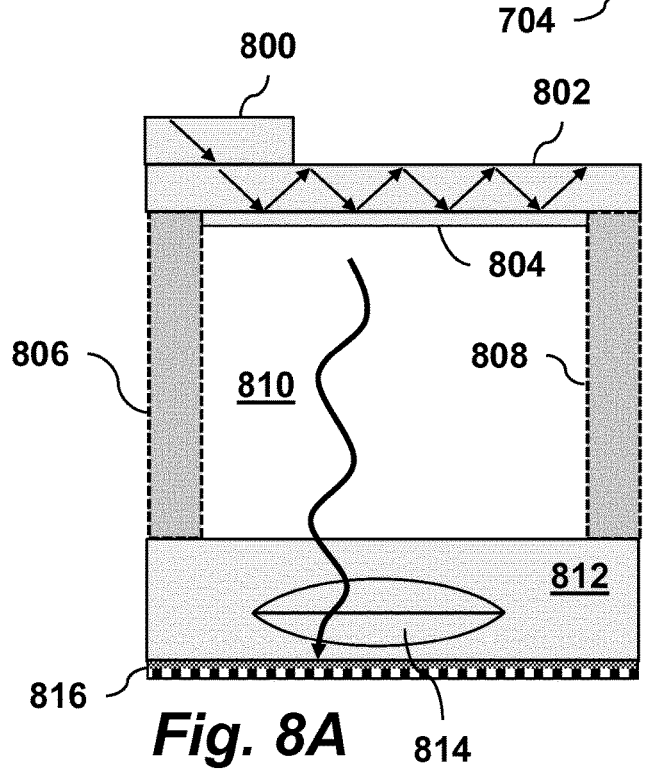
Figure 8B:
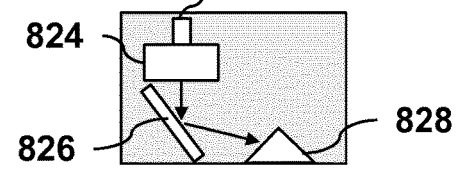
Figure 8C:
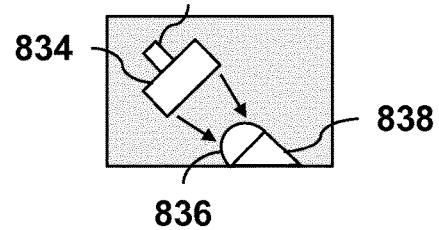
Figure 8D:
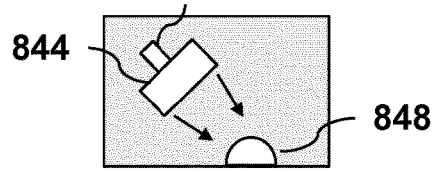
Figure 8E:
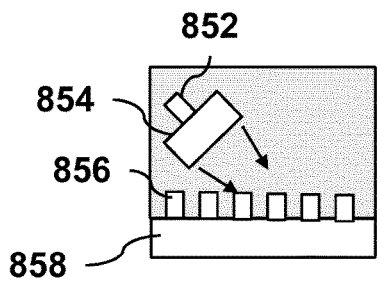
Figure 8F:
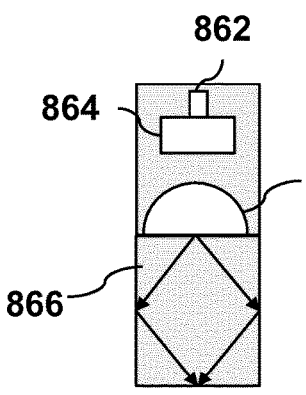

We refer to indirect TIR where the responsive layer is excited using secondary reflected lights within the substrate with optical properties. A system for indirect TIR has optical excitation which may be performed in both $L_x$ or $L_y$ directions and it has the following components: A light source, e.g., optical fiber, integrated LED, which can be mounted at a specific angle. A collimation/focusing system of the light composed of one or several lenses to maximize the collection of light from the light source, to properly shape the light source, and to limit the leakage of light in the system. Depending on the light coupling system strategy, the collimation/focusing system can be mounted at a specific angle. A light coupling system to achieve indirect TIR. This can be done in various ways, as illustrated in the cross-sectional schematic diagrams of FIGS. 8B-F. In FIG. 8B, a light source 822 and collimation element 824 directs light to a mirror 826 which reflects the light at an angle required for TIR, and a prism 828, to couple the light into the substrate. In FIG. 8C, a light source 832 and collimation element 834 directs light to a lens 836 mounted on a prism 838, to couple the light into the substrate. The TIR angle depends on the orientation of the light path reaching the lens. In FIG. 8D, a light source 842 and collimation element 844 directs light to a lens 836 directly glued or molded on the substrate. In FIG. 8E, a light source 852 and collimation element 854 directs light to a grating 856 deposited or created on part of the substrate 858, excluding the sensing area. In FIG. 8F, a butt-coupling strategy, a light source 862 and collimation element 864 directs light directly into the substrate 866. To ensure/improve light coupling efficiency, a lens 868 can be mounted/molded at the interface with the substrate. These techniques use indirect TIR excitation.

Techniques for direct TIR excitation are shown in FIGS. 9A-9C. In these embodiments, the biosensing layer is excited using the primary reflected light from the substrate with optical properties. Optical elements are used to prevent the excitation light to reach the light detection chip. In FIG. 9A, a light source 902, e.g., optical fiber or integrated LED, produces light, and a collimation/focusing system 904 is composed of one or several lenses to maximize the collection of light from the light source, to properly shape the light source, and to limit the leakage of light in the system. The collimated light then passes through a light coupling system, in this case a mirror 906 and prism 908. To achieve direct TIR, the light is coupled on the substrate with optical properties 910 and reflected directly from beneath the molecular responsive layer 912. The mirror directs the light to the desired angle, and the prism couples the light to the substrate. In FIG. 9B, a light source 922, e.g., optical fiber or integrated LED, produces light, and a collimation/focusing system 924 is composed of one or several lenses to maximize the collection of light from the light source, to properly shape the light source, and to limit the leakage of light in the system. The collimated light then passes through a light coupling system, in this case a lens 926 mounted on a prism 928 (or a single molded piece). To achieve direct TIR, the light is coupled on the substrate with optical properties 930 and reflected directly from beneath the molecular responsive layer 932. The lens is used to focus the light and the prism for coupling the light into the substrate. In FIG. 9C, a light source 942, e.g., optical fiber or integrated LED, produces light, and a collimation/focusing system 944 is composed of one or several lenses to maximize the collection of light from the light source, to properly shape the light source, and to limit the leakage of light in the system. The collimated light then passes through a light coupling system, in this case a lens 948. To achieve direct TIR, the light is coupled on the substrate with optical properties 950 and reflected directly from beneath the molecular responsive layer 952.

When using TIR, the excitation light is confined to a few hundreds of nanometers in the responsive layer. Although this is advantageous for the reduction of the light scattered from the background, the signal scattered from plastic particles may be not sufficient to resolve the motion of particles with the required accuracy. A strategy to overcome this problem is to let some light travel through the responsive layer. In order to limit the light scattered from the background, the light needs to be directed with an angle below the critical angle for TIR, but above the angle determined by the numerical aperture (NA) of the imaging system used. Moreover, optical elements can be added in order to prevent the excitation light to reach the light detection chip. We will refer to this strategy as high angle (HA) illumination. This can be achieved with the same excitation strategies as described above, provided that the excitation angle is larger than the critical angle for TIR.

We now turn to several imaging strategies. FIG. 10 is a cross-sectional schematic illustration of an embodiment of the invention using a set of lenses for imaging onto the sensor of the device. The top substrate 1000 with biosensing surface 1002 produces light that propagates through gap region 1008 between separation components 1004, 1006. The light then propagates through lens 1010 and is detected by sensor 1012. The molecular process at the biosensing surface 1002 is transduced into a detectable signal with an optical mechanism. The optical mechanism can involve a change of emission and/or absorption properties, a change of a coordination parameter of a particle, or a change of a scattering intensity.

In order to quantify the generated signal, the light from the responsive layer is guided to or imaged on a light detection chip using a set of optical components.

The choice of the optical components depends on:
- The transduction method (e.g., change of a scattering intensity, change of a coordination parameter).
    - For an optical mechanism involving a change of a coordination parameter of a particle, the particle imaging spot on the detection chip should be at least 2×2 pixels, in order to get the required spatial resolution for analysis.
    - For an optical mechanism involving a change of a scattering intensity of a plasmonic particle, it is required to record an image of the particle with a signal-to-noise-ratio (SNR) relative to changes of light intensity greater than 3, which corresponds to a SNR of about 300. This requires a sufficient amount of photon counting on the detection chip and the minimization of the noise in the system, e.g., the signal generated by the background.
- The miniaturization requirements. The size along the imaging axis depends on the intended use of the device. The in-body application is the most stringent in terms of miniaturization, with a maximum dimension in one direction of a few millimetres (<10 mm).

FIG. 11 is a cross-sectional schematic illustration of an embodiment of the invention using a set of rigidly coupled lenses for imaging onto the sensor of the device. The top substrate 1100 with biosensing surface 1102 produces light that propagates through gap region 1108 between separation components 1104, 1106. The light then propagates through lenses 1110, 1112 and is detected by sensor 1114. The rigidity of the system, with possible advantages for the production of a BCM unit; is increased by:
- Rigidly coupling the lens 1110 on the bottom substrate surface. This can be realized by assembly of the components or by injection molding.
- Rigidly coupling a lens 1112 in front of the light detection chip 1114. This can be done by attaching the lens to the chip (protected with an optically transparent layer).

FIG. 12 is a cross-sectional schematic illustration of an embodiment of the invention using lensless imaging onto the sensor of the device. The top substrate 1200 with biosensing surface 1202 produces light that propagates through gap region 1208 between separation components 1204, 1206. In this lensless imaging case, the distance between the biosensing surface 1202 and the light detection chip 1212 is sufficiently small that the light received from the sensitive layer 1202 gives a signal that is higher than the noise of the detection chip 1212. Additional components 1210 can be added to improve image quality (e.g., a metal grid).

FIG. 13A-13C are cross-sectional schematic figures illustrating embodiments with examples of rigidly coupled imaging systems. In FIG. 13A, a top substrate 1300 with biosensing surface 1302 is mounted to separation components 1304, 1306 which create gap region 1308. A rigid structure 1310 rigidly connects optical elements 1312 and detection chip 1314 to the lower substrate, top substrate 1320, and/or to separation components 1304, 1306. The rigid structure can have the secondary function of isolating the optical and electric components from the biological fluids. In FIG. 13B, a top substrate 1320 with biosensing surface 1322 is mounted to separation components 1324, 1326 which create gap region 1328. A rigid structure 1330 rigidly connects optical elements 1332, 1333 and detection chip 1334 to the lower substrate, top substrate 1320, and/or to separation components 1324, 1326. The optical element 1333 is rigidly connected to the light detection chip, e.g., using an optically transparent layer 1336 which may function as spacer to position the lens at the right distance to the light detection chip. The layer may also function as a protective layer. The optical element 1332 is rigidly connected to the bottom substrate. A strategy to increase the distance tolerance needed to image the biosensing surface is to position the lenses at a distance to the sensing layer and the detection chip equal to the focal length of the lenses, respectively. This creates parallel light rays between the lenses. In this way, a change of distance between the two lenses has no influence on the sharpness of the image of the particles on the imaging sensor. In FIG. 13C, a top substrate 1340 with biosensing surface 1342 is mounted to separation components 1344, 1346 which create gap region 1348. A rigid structure 1350 rigidly connects detection chip 1352 to the lower substrate, top substrate 1340, and/or to separation components 1344, 1346. In this embodiment, there are no lenses.

The relative positions of the responsive layer, the first imaging lens, the second imaging lens, the detection chip and the focal length of the two lenses will determine the field of view of the responsive layer imaged and the total magnification of the imaging system. As an example, by placing the biosensing surface in the focus of a lens, and by placing the sensing chip in the focus of a second lens, then the distance between the two lenses has no influence on the sharpness of the image of the particles on the imaging sensor, and the magnification is given by the ratio between the focal length of lenses. Depending on the cross-sectional size of the lens components, additional components may be used in order to prevent the light not captured by the lenses from reach the detector.

FIGS. 14A-14B are cross-sectional views of parts of an embodiment, illustrating measurement of a reference light intensity. It can be advantageous to measure a reference light intensity, e.g., the power of the light source, or a reference output level, in order to calibrate the power detected by the imaging sensor. As shown in FIG. 14A, a reference light intensity can be measured e.g., by using a light detection element 1404, e.g., a photodiode. An optical element, e.g., a trapezoidal prism 1402 couples the light out from the substrate 1400 and the light detection element 1404 collects that light. Alternatively, as shown in FIG. 14B, a light detection element 1402 is placed on the side of the substrate 1400. Moreover, fiducial markers can be embedded in the substrate in order to measure the intensity of the excitation light and to correct for drift in the system.

General Approaches to Manufacture the Device:

The device can be made by several techniques known in the art. For example, waveguiding, diffraction, and fluidic structures may be produced by thin-film techniques (e.g., spin-coating, evaporation, etching). Cartridge and optical components may be produced from optically transparent materials, e.g., glass or polymer. Components may be produced by patterning techniques (e.g., lithography, contact printing, microcontact printing, non-contact printing, self-assembly), additive manufacturing (e.g., 3D printing), joining (e.g., gluing, adhesive tape), assembly, automated placement, molding, over-molding, drop casting, curing (e.g., optical, thermal). Other possible techniques are bio-patterning, bio-deposition, bio-conjugation, physisorption, freeze drying, irradiation, packaging, sealing.

The optical system should be designed to give a high optical excitation efficiency of the sensing layer and a high detection efficiency of light emitted from the sensing layer (e.g., scattering or luminescence). This involves taking into account in the detection optics e.g., the thickness and refractive index of the material inside the gap, and the thickness and refractive index of the substrate that forms the opposite surface of the gap region.

The technology described herein—an optical continuous monitoring (BCM) unit—will allow for the continuous monitoring of biomarkers using affinity-based methods. This approach will allow to expand the range of biomarkers that nowadays can be measured, e.g., toward small molecules, electrolytes, metabolites, drugs, hormones, peptides, proteins, nucleic acids, etc. Moreover, in-vivo applications are very demanding in terms of miniaturization. What we describe herein are strategies that will allow to integrate and miniaturize sensing methods for on/in-body continuous monitoring of biomolecules, by using (i) a geometry that allows sensing with diffusive analyte transport, (ii) sensing material, e.g., particles, that generate an optical biosensing signal, and (iii) a detection method that allows to analyse signals from the sensing material, e.g., signals of individual particles.

Nowadays, continuous biomolecular monitoring is commercially available for glucose, e.g., the continuous glucose monitoring sensors from Abbott, Medtronic, and Dexcom. These are based on the enzymatic conversion of glucose. The enzymatic approach is not suited for the detection of biomolecules in general, such as proteins and small molecules, because suitable enzymes are not available and because the analyte concentrations are much lower than glucose. A sensing principle based on molecular binding affinity will be much more widely applicable than enzymatic sensing.

The affinity- and particle-based technologies described herein have the potential to give a broad applicability to biomarkers and also give a high analytical performance, i.e., sensitivity, specificity, accuracy, rapidity and reliability.

Particles are very stable, produce a high optical signal and allow for single-molecule resolution. Furthermore, a system with single-particle and/or single-molecule resolution will allow the readout of many independent sensors in parallel (for good statistics) and time-dependent signal analysis (association and dissociation events, stochastic signal analysis, digital detection). With the latter, it is also possible to access the molecular information of the interaction, to record distributions of molecular properties and dynamical processes, and to record rare events. An advantage of operating with single-molecule resolution is that the sensor signals are immediately digital. This allows for the acquisition and processing of dynamic switching signals (even in equilibrium), drift correction, suppression of non-specific signals, internal calibration, etc.

The device and methods of this invention are applicable to many types of optically responsive sensing layers. Furthermore, the device and methods of this invention are applicable to on/in-body continuous monitoring, but also for monitoring near a patient (e.g., in a blood line), or for monitoring of other types of samples of which chemical or biochemical properties need to be measured regularly and/or automatically (e.g., water quality monitoring).

On operation, the sensor device is brought in contact with a system of interest, e.g., a biological system, to allow transport of analyte into the sensor. Optical excitation of the particles is performed, tuning the parameters for optimal signal to noise. Signals are recorded from the particles and then analyzed to determine the presence and/or concentration of analyte.

Various types of analytes and matrix materials may be used. Analytes could include, for example, small molecules, peptides, proteins, hormones, electrolytes, metabolites, macromolecules, nucleic acids, carbohydrates, lipids. Matrix materials could include, for example, interstitial skin fluid, blood, saliva, mucosal fluid, cerebrospinal fluid, environmental fluids, fluids in biotechnological processes; extracts or filtrates from these matrices.

Optical excitation wavelengths envisioned for the device are visible and near-visible. The implementation of the I/O interface and image analysis and recording system depends on the application. Sensors on or in the body preferably have a wireless interface, but in many applications a wired interface is acceptable and simpler.

The image processing and signal processing and data analysis techniques would include recognition of particles, selection of particles, counting of particles, tracking of particle intensity and/or position and/or motion pattern, particle state determination, detection of particle state change events, analysis of state change statistics, interpretation in terms of presence and/or concentration of analyte.

The invention claimed is:

1. A biosensing device for continuous monitoring of an analyte in a fluid matrix, the device comprising:
    an electromagnetic excitation element, a biosensing surface, an opposing surface, a separation component, a light collection optics, a light sensor, an image recording and analysis system, and an excitation control system;
    wherein the separation component is connected to the biosensing surface and to the opposing surface, forming a concave gap region between the biosensing surface and the opposing surface, such that the biosensing surface and the opposing surface are opposite to each other and have a separation of at most 1 mm, wherein the biosensing surface and opposing surface both have lengths of at most 3 mm;
    wherein the electromagnetic excitation element and the light sensor are positioned on opposite sides of the gap region;
    wherein the excitation control system provides control signals to the electromagnetic excitation element to produce electromagnetic signals;
    wherein the electromagnetic excitation element is optically coupled to the biosensing surface, and wherein the biosensing surface comprises biosensing particles sensitive to the electromagnetic signals from the electromagnetic excitation element, wherein an optical response of the biosensing particles to the electromagnetic signals is adapted to change in the presence of an analyte in the gap region;
    wherein the light collection optics couple light emitted from the biosensing particles on the biosensing surface to the light sensor; wherein the light sensor and light collection optics are positioned outside of the concave gap region;
    wherein the image recording and analysis system is connected to the light sensor and processes light signals from the biosensing particles to determine presence or absence or concentration of the analyte in the fluid matrix.

2. The biosensing device of claim 1 wherein the electromagnetic excitation element is optically coupled to the biosensing surface by the concave gap region.

3. The biosensing device of claim 1 wherein the electromagnetic excitation element is optically coupled to the biosensing surface by a waveguide.

4. The biosensing device of claim 1 wherein the concave region is an enclosed region, wherein the separation component comprises a porous material with pores of 500 nm or smaller.

5. The biosensing device of claim 1 wherein the concave region is an open region, with an entrance region opposite the separation component.

6. The biosensing device of claim 1 wherein the separation component rigidly connects to both the biosensing surface and to the opposing surface.

7. The biosensing device of claim 1 wherein the biosensing surface and the opposing surface have widths of at most 1 cm.

8. The biosensing device of claim 1 wherein the opposing surface is optically transparent.

9. The biosensing device of claim 1 wherein the biosensing surface, the opposing surface, the separation component, the light collection optics, and the light sensor form a rigidly connected collection of components.

10. The biosensing device of claim 1 wherein the light sensor is a pixelated sensor chip, and wherein the image recording and analysis system comprises an input-output interface to the pixelated sensor chip.

11. The biosensing device of claim 1 wherein the light collection optics comprise a lens solidly integrated on the opposing surface, outside of the concave gap region.

12. The biosensing device of claim 1 wherein the electromagnetic excitation element is optically coupled to the biosensing surface by an optical waveguide providing total internal reflection or high angle illumination.

13. The biosensing device of claim 1 wherein the biosensing particles are micro- or nano-meter size biosensors with biomolecular specificity and single-molecule resolution.

\* \* \* \* \*